(12) United States Patent
Holbrook et al.

(10) Patent No.: US 8,451,162 B2
(45) Date of Patent: May 28, 2013

(54) MICROWAVE DATUM TOOL

(75) Inventors: David S. Holbrook, Lexington, MA (US); Christopher P. Adams, Somerville, MA (US)

(73) Assignee: Walleye Technologies, Inc., Somerville, MA (US)

( * ) Notice: Subject to any disclaimer, the term of this patent is extended or adjusted under 35 U.S.C. 154(b) by 119 days.

(21) Appl. No.: 12/158,456

(22) PCT Filed: Dec. 19, 2006

(86) PCT No.: PCT/US2006/048365
§ 371 (c)(1),
(2), (4) Date: Oct. 6, 2008

(87) PCT Pub. No.: WO2007/075639
PCT Pub. Date: Jul. 5, 2007

(65) Prior Publication Data
US 2009/0153392 A1    Jun. 18, 2009

Related U.S. Application Data

(60) Provisional application No. 60/752,120, filed on Dec. 20, 2005.

(51) Int. Cl.
*G01S 13/06* (2006.01)
(52) U.S. Cl.
USPC ............................................... 342/22; 342/5
(58) Field of Classification Search
USPC .......................................................... 342/22
See application file for complete search history.

(56) References Cited

U.S. PATENT DOCUMENTS

| | | | |
|---|---|---|---|
| 3,102,232 A | | 8/1963 | Leonard |
| 3,289,207 A | | 11/1966 | Lent |
| 3,693,079 A | | 9/1972 | Walker |
| 4,707,652 A | | 11/1987 | Lowitz |
| 5,020,886 A | | 6/1991 | Takeda et al. |
| 5,389,944 A | * | 2/1995 | Collinge et al. .............. 343/910 |
| 5,457,394 A | * | 10/1995 | McEwan ...................... 324/642 |
| 5,512,834 A | * | 4/1996 | McEwan ...................... 324/642 |
| 5,541,605 A | * | 7/1996 | Heger ............................. 342/85 |
| 5,543,799 A | * | 8/1996 | Heger ............................. 342/85 |
| 5,854,603 A | * | 12/1998 | Heger ............................. 342/85 |
| 5,896,102 A | * | 4/1999 | Heger ............................. 342/85 |

(Continued)

OTHER PUBLICATIONS

International Search Report, Application No. PCT/US06/48365, Dated Mar. 20, 2008.

(Continued)

*Primary Examiner* — John B Sotomayor
*Assistant Examiner* — Matthew M Barker
(74) *Attorney, Agent, or Firm* — Reza Mollaaghababa; Pepper Hamilton LLP

(57) ABSTRACT

In one aspect, a measurement system is disclosed that includes a source of microwave radiation having one or more wavelengths capable of penetrating through a visibly opaque obstruction, e.g., a wall. The source can be movably positioned on one side of the obstruction for illuminating thereof. The system can further include a microwave reflecting element disposed on another side of the obstruction, where the reflecting element is capable of reflecting at least a portion of the radiation transmitted through the obstruction. A plurality of radiation sensors are positioned relative to the obstruction so as to differentially detect at least a portion of the reflected radiation transmitted through the obstruction so as to determine a position of the source relative to the reflective element.

24 Claims, 4 Drawing Sheets

U.S. PATENT DOCUMENTS

| | | | |
|---|---|---|---|
| 5,933,120 A | 8/1999 | Manasson et al. | |
| 6,133,875 A * | 10/2000 | Kishimoto | 342/375 |
| 6,242,726 B1 | 6/2001 | Harris et al. | |
| 6,242,740 B1 * | 6/2001 | Luukanen et al. | 250/353 |
| 6,417,502 B1 * | 7/2002 | Stoner et al. | 250/208.1 |
| 6,473,049 B2 | 10/2002 | Takeuchi et al. | |
| 6,480,141 B1 | 11/2002 | Toth et al. | |
| 6,493,126 B1 | 12/2002 | Iizuka et al. | |
| 6,660,193 B2 | 12/2003 | Myhre | |
| 6,687,036 B2 | 2/2004 | Riza | |
| 6,696,827 B2 | 2/2004 | Fazekas et al. | |
| 6,703,944 B1 | 3/2004 | Obradovich | |
| 6,736,004 B2 * | 5/2004 | Evans et al. | 73/146 |
| 6,747,536 B1 | 6/2004 | Miller, Jr. | |
| 6,748,797 B2 | 6/2004 | Breed et al. | |
| 6,777,684 B1 * | 8/2004 | Volkov et al. | 250/341.1 |
| 6,844,713 B2 | 1/2005 | Steber et al. | |
| 7,605,743 B2 * | 10/2009 | Skultety-Betz et al. | 342/22 |
| 7,626,400 B2 * | 12/2009 | Holbrook et al. | 324/642 |
| 7,724,175 B2 * | 5/2010 | Mahler et al. | 342/22 |
| 2004/0255477 A1 | 12/2004 | Levine et al. | |
| 2005/0078303 A1 | 4/2005 | Murray | |
| 2005/0104603 A1 | 5/2005 | Peschmann et al. | |
| 2006/0061504 A1 * | 3/2006 | Leach et al. | 342/22 |
| 2008/0204322 A1 * | 8/2008 | Oswald et al. | 342/465 |
| 2009/0033539 A1 * | 2/2009 | Zemany | 342/22 |
| 2009/0295618 A1 * | 12/2009 | Beeri et al. | 342/22 |

OTHER PUBLICATIONS

International Preliminary Report on Patentability for Application No. PCT/US2006/048365, dated Jun. 24, 2008. (7 pages).

* cited by examiner

MICROWAVE DATUM TOOL

BACKGROUND

The present invention relates generally to measurement systems and methods, and more particularly, to such systems and methods that can be utilized to project reference datums through visually opaque objects, e.g., walls.

In the field of surveying, several well-known methods can be employed for implementing a variety of measurements between two or more points. These conventional methods, however, suffer from a number of shortcomings. For example, direct (point to point) measurements will not work if a measurement path between points cannot be penetrated with an infrared or a visible light beam. X-ray systems exist to image through and inside opaque objects. However, the use of such X-ray systems is typically limited as they are expensive, and can be potentially hazardous.

Hence, there exists a need for enhanced methods and systems for projecting reference datums through visually opaque objects, such as walls. There is also a need for such methods and systems that can be employed in the field of construction, as well as in other fields.

SUMMARY

In one aspect, the present invention employs a beam of microwave radiation to penetrate an obstruction, e.g., a visibly opaque wall, separating two locations to generate a reference between those locations. Many materials typically utilized in construction are transparent to microwave radiation of appropriate frequency. A transmitted reference beam having one or more appropriate frequency components can be projected through a visually opaque obstruction, e.g., a wall, to interact with a positionally and/or angularly sensitive detection device that can sense the transmitted beam. Some embodiments of the invention operate in a single-pass mode in which a radiation beam is transmitted once through the obstruction, e.g., a wall, and is sensed by a detection device (e.g., a plurality of sensors operating in a differential mode). Alternatively, other embodiments of the invention operate in a double-pass mode in which a radiation beam (e.g., microwave beam) emitted by a microwave source passes through the obstruction (e.g., a wall), reflects from a reference device, passes back through the obstruction and is positionally sensed.

In another aspect, the invention provides a measurement system that includes a source of microwave radiation having one or more wavelengths capable of penetrating through a visibly opaque obstruction, e.g., a wall. The source can be movably positioned on one side of the obstruction for illuminating thereof. The system can further include a microwave reflecting element disposed on another side of the obstruction, where the reflecting element is capable of reflecting at least a portion of the radiation transmitted through the obstruction. A plurality of radiation sensors are positioned relative to the obstruction so as to detect, e.g., differentially, at least a portion of the reflected radiation transmitted through the obstruction to determine a position of the source relative to the reflective element.

In a related aspect, the radiation source generates radiation with one or more wavelengths in a range of about 1 GHz to about 24 GHz (e.g., in a range of about 1 to about 2 GHz, or in a range of about 10 GHz to about 24 GHz) or any other suitable wavelength range. Some examples of suitable microwave sources include, without limitation, Gunn oscillators, magnetrons, IMPATT diodes, Dielectric Resonator Oscillators (DROs), MIMICs or other suitable radiofrequency oscillators.

In another aspect, the sensors are positioned relative to one another and the source so as to generate a differential null signal when the source, and more particularly the propagating direction of the radiation generated by the source, and the reflective element are substantially aligned. By way of example, the sensors can be positioned to generate a differential null signal when an optical axis of the source is aligned (its extension would intersect) with a reference location of the reflective element (e.g., its geometrical center).

In another aspect, a measurement system is disclosed that includes an electromagnetic imager adapted to generate images of an interior portion of a visibly opaque obstruction, where the imager comprises a source coupled to a focusing element for focusing radiation directed to a proximal side of the obstruction into an interior portion thereof and a detector for detecting at least a portion of the radiation propagating back from the obstruction. The system further includes a reflective focusing element disposed on a distal side of the obstruction for reflecting at least a portion of the radiation propagating through the obstruction. The detector detects at least a portion of the reflected radiation for determining an alignment of the source relative to the reflective element.

In a related aspect, the obstruction comprises a wall, and the reflective focusing element has a focal length of about ¼ of the wall's thickness.

In another aspect, a measurement system is disclosed that comprises a source of radiation adapted to generate a radiation beam having at least one wavelength capable of penetrating an obstruction (e.g., a visibly opaque one), where the source is movably positioned on one side of the obstruction for illuminating thereof with said radiation beam. The system further includes at least two sensors positioned on another side of the obstruction such that each sensor detects at least a portion of radiation transmitted through the obstruction so as to determine a position of said source relative to a reference point on said obstruction.

In a related aspect, in the above system, the sensors are adapted to differentially detect the radiation. For example, the sensors are adapted to generate a null signal when the source is aligned with said reference point.

In another aspect, the radiation source is capable of generating radiation with one or more frequency components in a range of about 1 GHz to about 24 GHz, e.g., in a range of about 10 GHz to about 20 GHz.

In another aspect, the invention provides a measurement method, which comprises movably disposing a radiation source on one side of a visibly opaque obstruction, said source generating radiation having at least one wavelength capable of penetrating through the obstruction. The method further calls for associating a reference element to a location at an opposed side of the obstruction, where the element is reflective to said at least one wavelength. A radiation beam having said wavelength is directed from the source to the obstruction such that at least a portion of said radiation penetrates the obstruction to illuminate said reflective element, and at least a portion of radiation reflected by the element is detected, e.g., differentially, at two or more spatially separate locations so as to determine a position of the source relative to the reflective element.

Further understanding of various aspects of the invention can be obtained by reference to the following detailed

DETAILED DESCRIPTION

The term "visibly opaque obstruction," as used herein, generally refers to a piece of material that substantially (or completely) blocks the passage of visible radiation (e.g., radiation having wavelengths in a range of about 400 nm to about 700 nm) therethrough. By way of example, a beam of light can lose more than about 90% of its intensity as it passes through the obstruction. Without loss of generality, in the following embodiments, the visibly opaque obstruction is assumed to be a wall. It should, however, be understood that the measurement systems and methods of the invention can be employed to project reference datums through other types of obstructions.

Figure 1A:
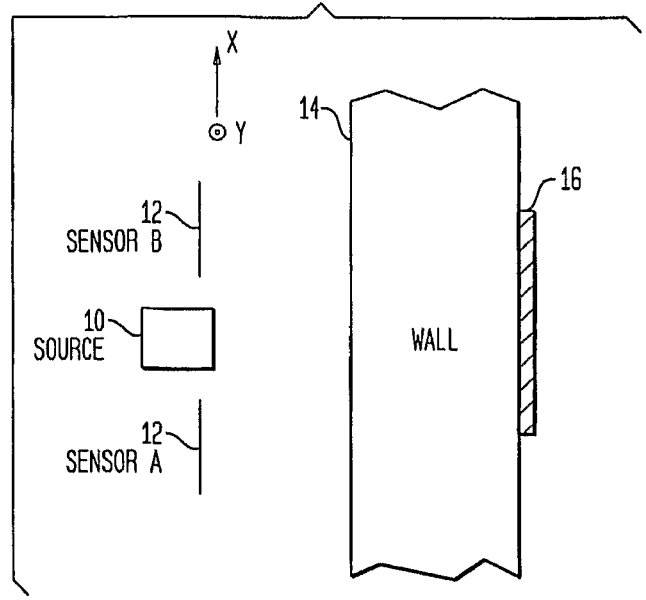
FIG. 1A schematically depicts an exemplary measurement system in accordance with one embodiment of the invention, FIG. 1B schematically depicts the propagation of radiation from the source in the measurement system of FIG. 1A via a proximal side of the wall into its interior to be reflected by a reflecting element disposed at a distal side of the wall, FIG. 2 schematically depicts an exemplary measurement system in accordance with another embodiment of the invention in which a source and a detector are disposed on the same side of an obstruction, FIG. 3 schematically depicts geometrical disposition of a source and four detectors of an exemplary measurement system according to an embodiment of the invention relative to one another, FIG. 4 schematically depicts a microwave source and four sensor channels suitable for use in some embodiments of the invention, FIG. 5 schematically depicts the profile of a measurement tool according to one embodiment of the invention having an interface providing visual indicators for indicating direction to null, FIG. 6 schematically depicts an imager incorporating a measurement system according to one embodiment of the invention for referencing coordinates on the back of a wall to those on the front, in which the MD reflector has a focal length that is about ¼ of the thickness of the wall, and FIG. 7 schematically depicts another embodiment of the invention in which a single pass of microwave radiation through an obstruction, e.g., a wall, is employed to align a radiation beam illuminating the obstruction from one side with a coordinate point on another side of that obstruction.
Figure 1B:
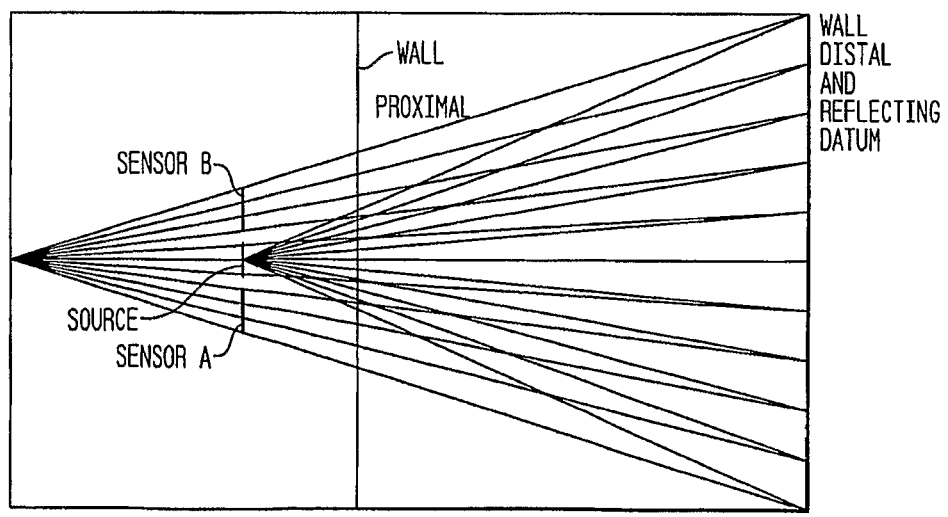

FIGS. 1A and 1B schematically depict an exemplary measurement system that comprises a measurement tool in accordance with one embodiment of the invention that can operate in a double-pass mode. The tool includes a radiation source 10 (a source of microwave radiation in this embodiment) and a radiation detector 12 that can be movably disposed on a proximal side of a wall 14. The microwave radiation source projects a beam of microwave radiation through the proximal side of the wall. A reflecting microwave optical device 16 (herein also referred to as the Microwave Datum or MD) is placed on the distal side of the wall, centered on the measurement point of interest. By way of example, the MD can comprise a reflecting Fresnel Zone Plate (FZP) with a focal distance chosen to be slightly longer than the thickness of the wall. For example, the MD can be a flat sheet typically composed of thin metal foil in a series of concentric zones. An adhesive can be applied to a surface of such a flat MD to allow it to be readily attached to the wall surface. The measurement tool can then be placed against the proximal surface of the wall and moved along that surface to sense the power reflected from the MD, thus determining the location of the MD on the distal side of the wall, as discussed in more detail below.

Preferably, the MD has a focal length chosen to image the source behind itself, as illustrated in FIG. 1B; that is, the image is at a focal distance slightly longer than the sum of the thickness of the wall and the known distance between the source and the proximal side of the wall. Generally, the preferred focal length can be calculated using the well known imaging relationship:

$$f = \frac{OI}{(O+I)} \quad (1)$$

where f is the focal length of a lens and O and I are the object and image distances respectively.

For the MD:

$$f_{MD} = \frac{(S+W)(S+W+d)}{(2S+2W+d)} \quad (2)$$

where $f_{MD}$ is the focal length of the MD, S is the distance from the source to the proximal side of the wall, W is the thickness of the wall, and d is a predetermined distance behind the source at which the source image is to be formed.

In some embodiments, when the measurement tool is centered on the datum, an alert signal is provided to the user. When the source and the datum are not aligned, one or more indicators (e.g., a set of arrows) on the tool indicate the direction of the datum position, that is, the direction in which the source should be moved to align it with the datum. In some embodiments, the relative position of the source and the datum is defined by a vector extending from a fiducial point on the source to a reference point on the datum. By way of example, in some embodiments, the source and the datum are considered aligned when an optical axis of the source (e.g., characterized by a central ray of a beam emitted by the source) is directed towards a reference point (e.g., the geometrical center) of the datum.

In this exemplary embodiment, the measurement system operates by differentially sensing a cone of microwave radiation rays forming a beam that is reflected from the MD. The tool's detector functions as a nulling sensor that provides directional information when off null (i.e., when not exhibiting a null signal) to allow the user to quickly converge on the null position. FIG. 1B farther illustrates the optical geometry in this embodiment. The source emits a cone of radiation that is transmitted through the wall to the MD. The MD retrofocuses the radiation power to a position behind the proximal surface of the wall. Before coming to focus, the power traversing through the space above the source is collected by sensor B's aperture and is sensed. The power below the source is likewise collected and sensed by sensor A. When the MD is located on the optical axis, the power sensed by sensor B is substantially equal to that sensed by sensor A. In this embodiment, a second pair of sensors (sensors C and D in FIG. 3) are located in and out of the page (along an axis perpendicular to one along which sensors A and B are disposed), thus resulting in a total of 4 sensors that are differentially connected to sense two degrees of freedom (X and Y).

Figure 3:
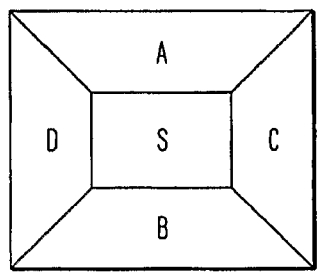

This geometry is illustrated in FIG. 3, which schematically shows the source and sensor channels as viewed from the distal side of the wall.

In this embodiment, the following sensing algorithm can be implemented in an electronic circuit to compute a normalized difference signal:

$$V_{Delta\ Y} = k(P_A - P_B)/(P_A + P_B) \quad (3)$$

where:
$P_A$=power sensed by channel A
$P_B$=power sensed by channel B
$V_{Delta\ Y}$=the output of the circuit with a given datum misalignment
K=a constant, and likewise:
$V_{Delta\ X} = k(P_C - P_D)/(P_C + P_D)$
where C and D represent the sensors into and out of the plane of the page.

The above algorithm produces an output of zero when the tool is aligned on the MD. The output swings from minus to zero and then plus as the tool is scanned across the MD position.

The focal distance and diameter of the MD can be easily tailored to accommodate various wall thicknesses. In general, thicker walls require MDs having longer focal lengths, in accordance with Equation (1). Furthermore, with thicker walls it is preferable for the MDs to have larger diameters. Generally, the diameter of the MD increases in proportion to thickness of the wall to maintain the cone angle of the light forming the image of the source. As measured by well known optical parameter f/#, the preferred cone angle is simply:

$$f/\#_{MD} = d/D, \quad (4)$$

where d is the predetermined distance behind the source at which the source image is to be formed and D is the desired diameter of the beam in the plane of the detectors. In some embodiments, D is preferably equal to the diameter of the circle that circumscribes the 4 detectors surrounding the source.

In some embodiments, the microwave detection method is a standard microwave technique known as frequency modulated continuous wave (FMCW). A single Gunn oscillator source, for example, including a resonant cavity provides microwave output power. This cavity is also connected to the 4 sensor channels to act as a local oscillator for detection (shown in FIG. 4). Each of the 4 sensor channels uses, for example, a Schottky diode for detection of the collected microwave power. In some embodiments, the tool is battery powered with a 4.5 to 9 V battery.

Figure 5:
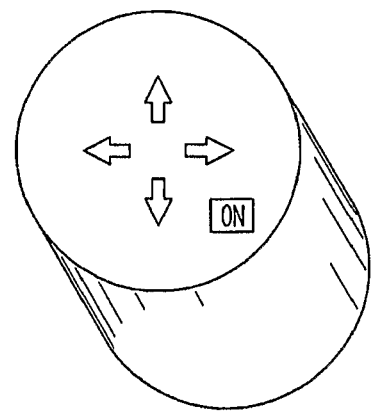

In some embodiments, the tool is fairly compact with approximate dimensions of, for example, 3" in diameter by 3" in height (shown in FIG. 5). Further, in some embodiments, the user interface includes an on/off button and visual indicators, e.g., 4 LEDs which light up to indicate direction to null. Upon reaching a null, the visual indicators provide a selected signal to the user to indicate alignment of the source with the MD, e.g., all 4 LEDs will blink. In some embodiments, the radiation source, the sensors, the user interface and the ancillary electronic circuitry are incorporated in a handheld housing.

In general, the frequency of operation depends on the type of material from which the obstruction, e.g., a wall, is formed. By way of example, in case of a drywall, some embodiments of the invention employ a radiation frequency in a range of about 10 GHz to about 24 GHz, as radiation in that frequency range exhibits good transmission through a drywall. In case of a wall formed of concrete, a lower frequency might be required. Scattering of the microwave beam by inhomogeneities in the concrete is reduced with a lower frequency microwave source (longer wavelength). For example, a radiation frequency in a range of about 1 to about 2 GHz can be employed for obstructions formed of concrete, as radiation in that frequency range transmits better through concrete. Moreover, in the case of concrete (and other cases when suitable), some embodiments employ a ¼ wavelength thickness of a low index of refraction material (plastic) to impedance match the transition of microwaves between air and (high index) concrete.

In addition, in many embodiments, the intensity of the radiation emitted by the source is selected such that the intensity of the radiation reaching the detectors (e.g., via one or two passages through the obstruction) is sufficient for an adequate signal-to-noise ratio of the detectors' outputs. By way of example, in some embodiments, the power output of the source is in a range of about 10 micro-Watts to about 10 milli-Watts, and the intensity of a radiation beam emitted by the source is in a range of about 10 micro-Watts per square centimeter to about 10 milli-Watts per square centimeter.

Figure 4:
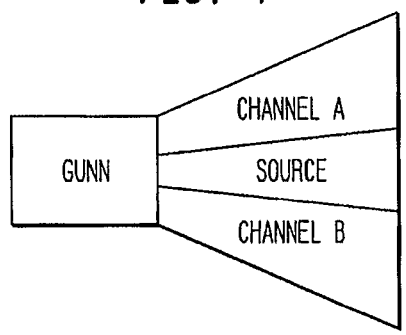

With reference to FIG. 4, in this exemplary embodiment, the geometry of the source and sensor horn antennas is chosen to allow a wide angular admittance of microwave beams without significant attenuation. This results in a small aperture width.

Although the above embodiments are implemented by employing a differential detection system, in other embodiments, a non-differential detection system can be utilized. For example, a source can be aligned with the MD by maximizing the power detected non-differentially by a detector as a function of the detector's position.

Figure 2:
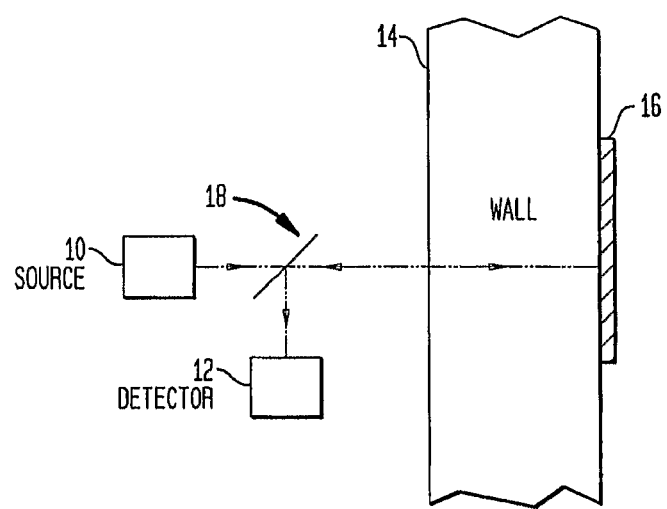

With reference to FIG. 2, in another embodiment, a radiation source 10 is optically coupled to a beam splitter 18 that passes the radiation from the source, through the wall, onto the MD 16. The beam splitter directs the back-propagating radiation, generated via reflection of the incident radiation by the MD, onto a detector 12. By way of example, the detector 12 can include a plurality of detecting modules that differentially detect the reflected radiation, e.g., in a manner discussed above, so as to provide an indication of the relative alignment of the source and the MD. The source, the beam splitter and the detector can be disposed in a portable housing that can be readily moved so as to align the source with the MD.

In some embodiments, the MD reflector is coated with a non-marring adhesive and hence it can be easily relocated on the distal side of the wall so as to function as a reference datum.

Figure 6:
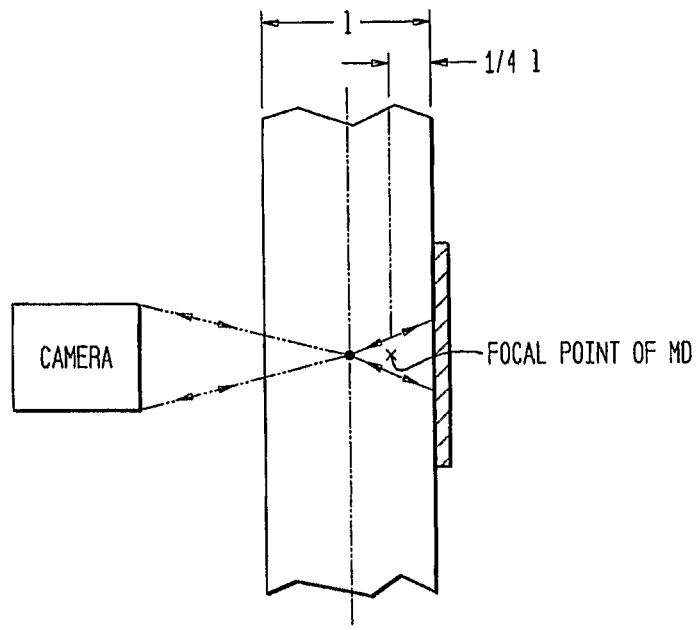

In another embodiment, a camera (imager), such as has been disclosed in a co-pending patent application Ser. No. 11/353,882 entitled "Electro-Magnetic Scanning Imager," filed on Feb. 14, 2006, which is herein incorporated by reference in its entirety, can be utilized in conjunction with the MD to reference coordinates on the back of an obstruction (e.g., a wall) to those on the front. By way of example, in one embodiment, the camera includes a radiation source that generates radiation that is capable of penetrating the wall (e.g., radiation with frequency components in a range of about 1 GHz to about 24 GHz). A focusing element coupled to the radiation source focuses the radiation onto an object plane within the wall, and directs at least a portion of the focused radiation propagating back from that object plane onto a detector of the camera. A scanning mechanism coupled to the focusing element causes scanning of the focused radiation on the object plane (in some embodiments, the mechanism provides scanning along one dimension and the movement of the camera by a user provides scanning in an orthogonal dimension). A processor maps the detected radiation to the scanned locations to generate an image of the object plane, which can then be presented to a user in a display module of the camera. In some embodiments, when utilized in conjunction with the MD, the camera scans the front of the wall and sees where the MD reflector is. In such a case, the focal length of the MD is preferably chosen to be ¼ of the wall thickness so that the MD would provide a 1:1 image of radiation from the camera focused about half way into the wall, as shown schematically in FIG. 6. In this manner, the coordinates on the back of the wall can be referenced to those on the front.

Metals generally reflect or scatter microwave radiation at different frequencies. In some embodiments of the invention, the attenuation of microwave radiation through a path can be assessed to determine whether that path is free (or at least substantially free) of metals. For example, in the above double-pass embodiment, the intensity of microwave radiation reflected from the MD and detected by the sensors can be compared with the intensity of the radiation illuminating the wall to determine whether the path of the radiation through the wall is substantially free of metal.

Figure 7:
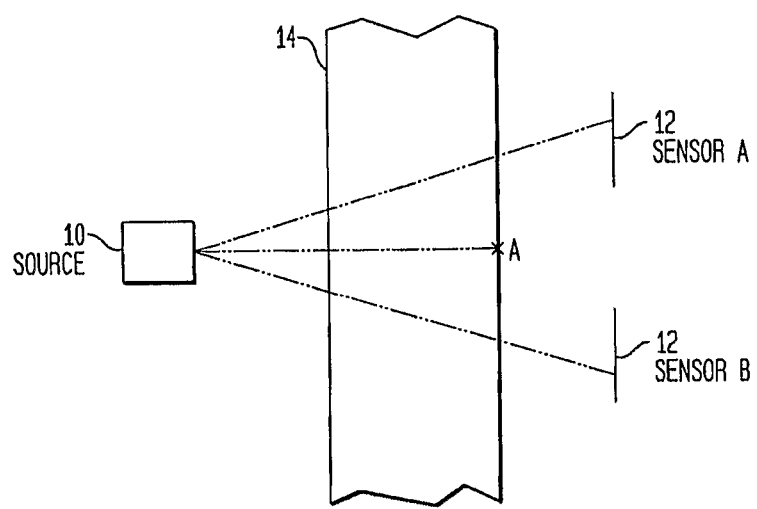

FIG. 7 schematically depicts another embodiment of the invention in which a single pass of microwave radiation through an obstruction, e.g., a wall, is employed to align a radiation beam illuminating the obstruction from one side with a coordinate point on another side of that obstruction. This exemplary embodiment includes a microwave source 10 that generates radiation with wavelengths suitable for penetration through the wall 14. A detector 12, which comprises four sensors (two of which A and B are shown), symmetrically disposed relative to one another, differentially detects the radiation that has passed through the wall. For example, the detector can be aligned with a coordinate point A on the back surface of the wall by detecting a null signal generated by the detector when the central ray of a cone of diverging microwave radiation from the source illuminating the wall is aligned with that coordinate point.

Those having ordinary skill in the art will appreciate that various modifications can be made to the above embodiments without departing from the scope of the invention.

What is claimed is:

1. A measurement system, comprising
   a source of radiation having one or more wavelengths capable of penetrating through an obstruction, said source being movably positioned on one side of the obstruction for illuminating thereof with said radiation,
   a reflecting imaging element adapted for placement at a measurement location of interest on another side of the obstruction, said reflecting element being capable of reflecting at least a portion of the radiation transmitted through the obstruction, and
   a plurality of radiation sensors positioned relative to the obstruction so as to detect at least a portion of the reflected radiation transmitted through the obstruction so as to determine a position of said source relative to said reflective element
   wherein said reflecting imaging element is configured to retro-focus the radiation to form an image of the source.

2. The system of claim 1, wherein said obstruction is visibly opaque.

3. The system of claim 1, wherein said sensors differentially detect said reflected radiation.

4. The system of claim 1, wherein said sensors are positioned as so to generate a null signal when said source and said reflective element are substantially aligned.

5. The system of claim 1, wherein said source generates microwave radiation with one or more frequency components in a range of about 1 GHz to about 24 GHz.

6. The system of claim 5, wherein said source generates microwave radiation with one or more frequency components in a range of about 1 GHz to about 2 GHz.

7. The system of claim 5, wherein said source generates microwave radiation with one or more frequency components in a range of about 10 GHz to about 20 GHz.

8. The system of claim 1, wherein said obstruction comprises a wall and wherein said reflecting element is adapted for attachment to a surface of the wall.

9. The system of claim 1, wherein said reflecting imaging element forms the image of the source at an image distance greater than a distance between the source and the reflecting element.

10. The system of claim 1, wherein said reflecting imaging element comprises a Fresnel Zone Plate.

11. The system of claim 1, wherein the system comprises one or more indicators that indicate the direction of the location of interest at which the reflecting element is placed.

12. A measurement method, comprising
    movably disposing a radiation source on one side of a visibly opaque obstruction, said source generating radiation having at least one wavelength capable of penetrating through said obstruction,
    associating a reference imaging element to a location at an opposed side of said obstruction, said element being reflective to said at least one wavelength and being configured to retro-focus at least a portion of radiation incident thereon to form an image of said source,
    directing a radiation beam having said wavelength from the source to the obstruction such that at least a portion of said radiation penetrates the obstruction to illuminate said reference element, and
    detecting at least a portion of radiation reflected by said element at two or more spatially separate locations so as to determine a position of the source relative to the reflective element.

13. The method of claim 12, further comprising selecting said at least one frequency to be in a range of about 1 GHz to about 24 GHz.

14. The method of claim 13, further comprising selecting said at least one frequency to be in a range of about 10 GHz to about 20 GHz.

15. The method of claim 12, wherein said detecting step comprises differentially detecting said reflected radiation at said two or more locations.

16. The method of claim 12, wherein the step of associating said reflective element with a location comprises disposing said reflective element on a surface of said obstruction.

17. The method of claim 16, wherein said obstruction comprises a wall and disposing said reflective element on a surface of said obstruction comprises attaching the reflective element to a surface of the wall.

18. The method of claim 12, wherein the step of directing the radiation further comprises positioning the source so as to illuminate said reflective element by the radiation beam.

19. The method of claim 12, wherein determining a position of the source relative to the reflective element comprises determining an angle of incident of said radiation beam on said reflective element.

20. The method of claim 12, wherein said location is a measurement location of interest.

21. The method of claim 12, wherein said reflecting imaging element forms the image of the source at an image distance greater than a distance between the source and the reflecting element.

22. The method of claim 12, wherein said reflecting imaging element comprises a Fresnel Zone Plate.

23. The method of claim 12, further comprising one or more indicators that indicate the direction of the location of the reflecting element.

24. A measurement system, comprising
- a source of radiation having one or more wavelengths capable of penetrating through an obstruction, said source being movably positioned on one side of the obstruction for illuminating thereof with said radiation,
- a reflecting imaging microwave optical device disposed on another side of said obstruction, said reflecting microwave optical device being capable of reflecting at least a portion of the radiation transmitted through the obstruction and being configured to retro-focus the radiation to form an image of said source, and
- a plurality of radiation sensors positioned relative to the obstruction so as to detect at least a portion of the reflected radiation transmitted through the obstruction so as to determine a position of said source relative to said reflecting microwave optical device.

* * * * *